United States Patent [19]
Susuki et al.

[11] 3,988,218
[45] Oct. 26, 1976

[54] PROCESS FOR RECOVERING ALKYL SULFONIC ACID FROM PHOTOSULFOXIDATION REACTION MIXTURE

[75] Inventors: Rinnosuke Susuki, Tokyo; Sadao Toyoda, Funabashi; Keiji Endo, Tokyo, all of Japan

[73] Assignee: Lion Fat & Oil Co., Ltd., Tokyo, Japan

[22] Filed: Dec. 29, 1972

[21] Appl. No.: 319,319

Related U.S. Application Data

[63] Continuation of Ser. No. 70,306, Sept. 8, 1970.

[30] Foreign Application Priority Data

Sept. 11, 1969  Japan .................. 44-72136

[52] U.S. Cl. .................... 203/39; 203/91; 260/504 R; 260/513 R
[51] Int. Cl.² ........................... B01D 3/10
[58] Field of Search .............. 260/513, 504, 686; 203/96, 95, 91, 92, 39

[56] References Cited
UNITED STATES PATENTS

| | | | |
|---|---|---|---|
| 2,523,490 | 9/1950 | Adams et al. ............... | 260/513 |
| 3,507,909 | 4/1970 | Blackwell ...................... | 260/513 |

FOREIGN PATENTS OR APPLICATIONS

| | | | |
|---|---|---|---|
| 803,558 | 1/1969 | Canada ......................... | 260/513 |
| 1,579,525 | 7/1969 | France .......................... | 260/513 |
| 6,506,488 | 3/1964 | Netherlands .................. | 260/513 |
| 1,144,128 | 3/1969 | United Kingdom ........... | 260/513 |
| 1,094,999 | 7/1966 | United Kingdom ........... | 260/513 |
| 1,194,699 | 6/1970 | United Kingdom ........... | 260/513 |

*Primary Examiner*—Norman Yudkoff
*Assistant Examiner*—J. Sofer
*Attorney, Agent, or Firm*—Woodhams, Blanchard and Flynn

[57] ABSTRACT

A process for recovering alkyl sulfonic acid from a photosulfoxidation reaction mixture of an alkane comprising the steps of: separating a major portion of the unreacted alkane contained in said reaction mixture by settling; subjecting thus treated reaction mixture to steam-distillation to remove the remaining portion of the unreacted alkane together with the sulfur dioxide therefrom; subsequently separating the sulfuric acid without heating from the resulting mixture by settling, thereby recovering the alkyl sulfonic acids.

4 Claims, 1 Drawing Figure

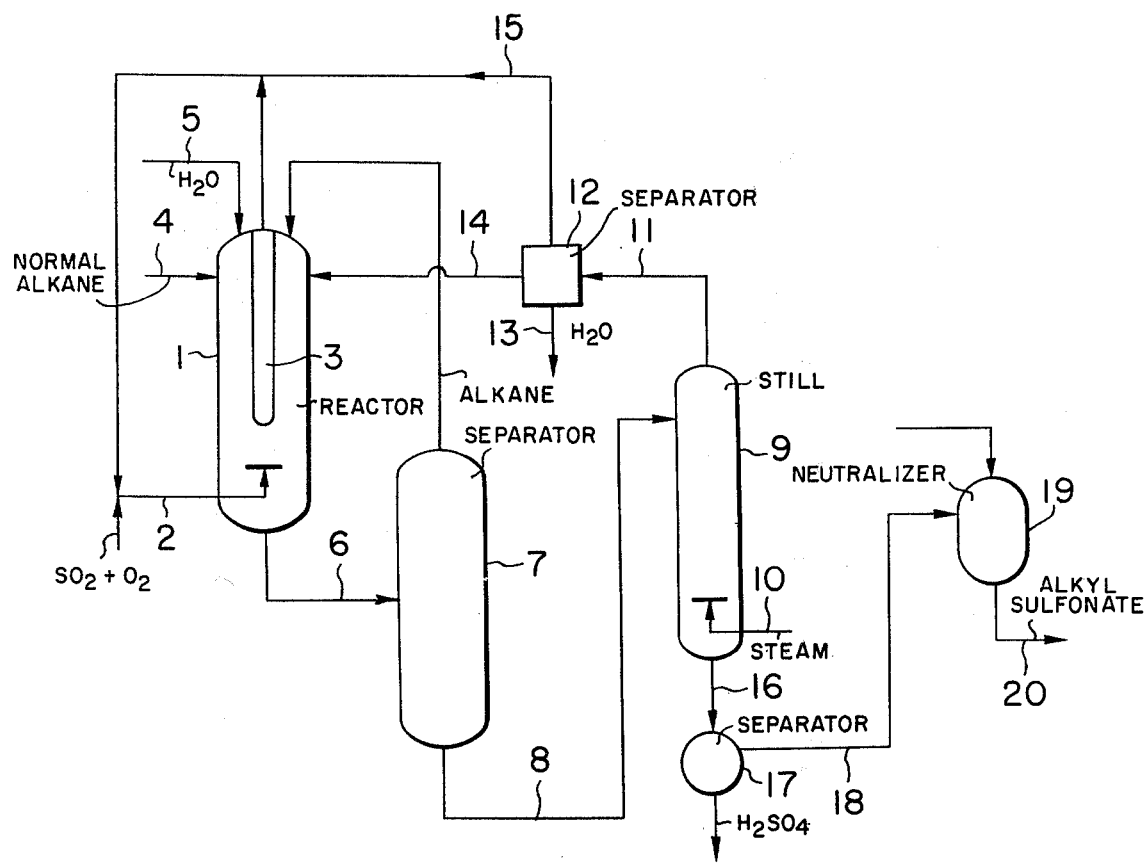

PROCESS FOR RECOVERING ALKYL SULFONIC ACID FROM PHOTOSULFOXIDATION REACTION MIXTURE

This is a continuation of application Ser. No. 70,306, filed Sept. 8, 1970.

BACKGROUND OF THE INVENTION a. Field of the Invention

The present invention relates to a novel method of preparing an alkyl sulfonic acid, and, more particularly, it relates to a novel process of recovering the intended alkyl sulfonic acid from a photosulfoxidation reaction mixture.

b. Description of the Prior Art

The alkyl sulfonic acids popular as surface active agents have usually been prepared by means of photosulfoxidation of an alkane. The conventional method of recovering alkyl sulfonic acids entails very complicated processes in order to obtain the intended product from a reaction mixture: namely, a major portion of the unreacted alkane is separated from the photosulfoxidation reaction mixture by settling; then, said mixture is first heated to evaporate the sulfur dioxide contained therein; subsequently, after concentration of the mixture by heating, the sulfuric acid is separated therefrom by settling; the mixture thus treated is neutralized and thereafter subjected to steam-distillation to separate alkane therefrom, whereby the intended alkyl sulfonic acids are recovered in the form of an alkali salt. Not only that, this method in the prior art involves knotty problems also from the aspect of the thermal efficiency, such as: it is necessary to cool, on the occasion of neutralizing an alkyl sulfonic acid, the reaction mixture concentrated by heating at the time of separating sulfuric acid therefrom; the steam-distillation process following the neutralization process brings about an increase in the viscosity of the reaction mixture as the separation of alkane progresses, making it necessary to heat the mixture again in order to control said viscosity; and so on.

SUMMARY OF THE INVENTION

In view of the foregoing drawbacks in the prior art, the present invention proposes a method of recovering the intended alkyl sulfonic acids from a photosulfoxidation reaction mixture through a more simple process. The method of preparing an alkyl sulfonic acid according to the present invention recovers the intended alkyl sulfonic acids in the form of sulfonic acid according to the invention, a major portion of the unreacted alkane is first separated from the reaction mixture resulting from the photosulfoxidation of an alkane; subsequently, the remaining portion of the unreacted alkane together with the sulfur dioxide is removed from the reaction mixture by means of steam-distillation; and the thus treated reaction mixture is thereafter merely left standing to let the sulfuric acid separate therefrom by settling, thereby obtaining alkyl sulfonic acids. Suitable alkanes which may be utilized in the process of this invention include, in particular, the alkanes containing from 10 to 26 carbon atoms.

According to the present invention, therefore, inasmuch as the viscosity of the reaction mixture at the time of removing the remaining portion of the unreacted alkane by means of steamdistillation is lower than that in the prior art, said steamdistillation can be performed by applying a comparatively low temperature (viz. usually at a temperature in the range of 80°–250° C, and preferably in the range of 100°–110° C), and, in addition, the separation efficiency on this occasion can also be improved. Furthermore, the steam-distillation conducted at a relatively lower temperature results in an improvement in the color of the alkyl sulfonic acids. Moreover, in the method of the present invention, since it is feasible to effect simultaneously the separation of unreacted alkane and sulfur dioxide, the thermal efficiency is enhanced and the calorie consumption may be reduced to about two-thirds as much as that in the prior art. Shown in the following Table 1 is a comparison between the method of the present invention and that of the prior art in respect of the separation process for the unreacted alkane and that for the sulfuric acid.

Table 1

| Condition | | Method | Prior Art | Present Method |
|---|---|---|---|---|
| Separation of Unreacted Alkane | Ability | (normal alkane g/hr) | 11 | 26 |
| | Amount of steam consumed | (g/normal alkane-g) | 9 | 3 |
| | Temperature | (° C) | 150 | 100 |
| | Color | (KL color 5 % sodium sulfonate aq. soln) | 400 | 250 |
| Separation of Sulfuric Acid | Temperature | (° C) | 140–150 | 100 |
| | Concentration of separated sulfuric acid | (wt %) | 65–70 | 70 |
| | Time for separating sulfuric acid | (min) | 30 | 10 |
| | Sulfuric acid separation | (wt %) | 88 | 90 |

As elucidated in the foregoing, one feature of the present invention lies in the process of simultaneously separating the remaining portion of the unreacted alkane and the sulfur dioxide from the reaction mixture (from which a major portion of said unreacted alkane has previously been separated by settling) by means of steam-distillation. As to said distillation, the conditions thereof are as listed in the following Table 2.

Table 2

| Item | Range Minimum | Range Maximum | Optimum | Reason for Limitation As to Minimum | Reason for Limitation As to Maximum |
| --- | --- | --- | --- | --- | --- |
| Distillation temperature (°C) | 80 | 250 | 100–110 | Distllation is costly | Color of the reaction product degenerates. |
| Distillation pressure (mm Hg) | 50 | 760 | 50–100 | Distillation and apparatus are costly. | Distillation is costly. |
| Concentration of sulfuric acid separated after the concentration (wt %) | 50 | 95 | 65–80 | Separation rate of sulfuric acid is poor | Color of the reaction product degenerates. |

BRIEF DESCRIPTION OF THE DRAWING

The appended drawing is a schematic representation of apparatus which may be utilized in practicing one embodiment of the present invention.

DESCRIPTION OF THE PREFERRED EMBODIMENTS

EXAMPLE 1

By means of stocking 5l of a normal alkane in a reactor 1 as shown in the appended drawing, introducing therein a reaction gas (prepared by mixing sulfur dioxide with oxygen gas at the rate of 2:1 by volume) at the rate of 600l per hour through the conduit 2, supplying the normal alkane and additive water through the conduit 4 and the conduit 5 respectively at the rate of 40l per hour and applying 100W high-pressure mercury lamp 3, photosulfoxidation was effected. The reaction mixture thus obtained was introduced, through the conduit 6, into the separation tank 7, where the reaction mixture was separated into unreacted normal alkane and heavy reaction mixture (comprising 30 Wt% of sulfonic acids, 30 Wt% of water, 10 Wt% of sulfuric acid, 28 Wt% of normal alkane and 2 Wt% of sulfur dioxide). This heavy reaction mixture was sent in the distillation tower 9, 5 cm in diameter and 30 cm in height, through the conduit 8, where steam-distillation was effected at 150° C by means of supplying steam superheated at temperature of 150° C, through the conduit 10, to said distillation tower, coupled with heating from the outside of the tower. Through the conduit 11, the distillate comprising normal alkane, water and sulfur dioxide was sent in the separation tank 12, where said distillate was separated into water to be directed to the conduit 13, normal alkane directed to the conduit 14, and sulfur dioxide directed to the conduit 15, respectively. The effluent consisting of sulfonic acids and sulfuric acid of a concentration of 70 wt.% sent from the distillation tower 9 through the conduit 16 to the separation tank 17 and was separated into sulfuric acid and sulfonic acid within said separation tank 17. The sulfonic acids resulting from the separation were sent in the neutralization tank 19 through the conduit 18, and alkyl sulfonates were obtained through the conduit 20.

The conditions for conducting the experiment in this example together with the result of experiment were as shown in the following Table 3.

Table 3

| Process | Condition | | Results |
| --- | --- | --- | --- |
| Separation by distillation | amount treated | (normal alkane g/hr) | 26 |
| | amount of steam | (g/normal alkane-g) | 3 |
| | temperature | (° C) | 150 |
| | pressure | (mmHg) | 160 |
| | removal rate of sulfur dioxide | (%) | 100 |
| Separation of sulfuric acid | temperature | (° C) | 150 |
| | concentration of separated sulfuric acid | (wt %) | 70 |
| | time for separation of sulfuric acid | (min) | 10 |
| | separation rate of sulfuric acid | (%) | 90 |
| Properties of separated sulfonic acid | sulfonic acids content | (wt %) | 80 |
| | normal alkane content | (wt %) | 0.5 |
| | sulfuric acid content | (wt %) | 2.7 |
| | water content | (wt %) | 16.8 |
| | sulfur dioxide | (wt %) | Only a trace observed. |
| | color | (KL color 5 % sodium sulfonate aq. sol) | 400 |

EXAMPLE 2

By means of employing a reaction mixture produced through the same operation as in Example 1, supplying said reaction mixture to the distillation tower 9, 5 cm in diameter and 30 cm in height, through the conduit 8, and introducing steam superheated at 130° C into said distillation tower through the conduit 10 coupled with heating from the outside of said tower, steam-distillation was effected at a temperature of 130° C. Through the conduit 11, the distillate comprising normal alkane, water and sulfur dioxide was sent in the separation tank 12, where said distillate was separated into sulfur dioxide, normal alkane and water. Sulfonic acids, together with sulfuric acid of a concentration of 65 Wt.%, were made to flow out through the conduit 16, and the sulfonic acids were separated from said sulfuric acid within the separation tank 17. Thus obtained sulfonic acids were subsequently neutralized in the neutralization tank 19, whereby there were obtained alkyl sulfonates.

The conditions for conducting the experiment in this example together with the result of experiment were as shown in the following Table 4.

Table 4

| Process | Condition | | Result |
|---|---|---|---|
| Separation by distillation | amount treated | (normal alkane g/hr) | 22 |
| | amount of steam | (g/normal alkane-g) | 7.5 |
| | temperature | (° C) | 130 |
| | pressure | (mmHg) | 760 |
| | removal rate of sulfur dioxide | (%) | 100 |
| Separation of sulfuric acid | temperature | (° C) | 130 |
| | concentration of separated sulfuric acid | (wt %) | 65 |
| | time for separatin of sulfuric acid | (min) | 10 |
| | separation rate of sulfuric acid | (%) | 80 |
| Properties of separated sulfonic acids | sulfonic acids content | (wt %) | 70 |
| | normal alkane content | (wt %) | 0.5 |
| | sulfuric acid content | (wt %) | 4.7 |
| | water content | (wt %) | 24.8 |
| | sulfur dioxide content | (wt %) | Only a trace observed. |
| | color (KL color 5 % sodium sulfonate aq. soln) | | 300 |

EXAMPLE 3

By means of employing a reaction mixture produced through the same operation as in Example 1, supplying said reaction mixture to the distillation tower 9, 5 cm in diameter and 30 cm in height, through the conduit 8, and introducing steam heated at 100° C into said distillation tower through the conduit 10 while maintaining the inner pressure of the tower at 50 mmHg and further applying heat from the outside of the tower, steam-distillation was effected at a temperature of 100° C. Through the conduit 11, the distillate comprising normal alkane, water and sulfur dioxide was sent in the separation tank 12, where said distillate was separated into sulfur dioxide, normal alkane and water.

Sulfonic acids, together with sulfuric acid of a concentration of 70 Wt.%, were made to flow out through the conduit 16, and the sulfonic acids were separated from said sulfuric acid within the separation tank 17. Thus obtained sulfonic acids were subsequently neutralized in the neutralization tank 19, whereby there were obtained alkyl sulfonates.

The conditions for conducting the experiment in this example together with the result of experiment were as shown in the following Table 5.

Table 5

| Process | Condition | | Result |
|---|---|---|---|
| Separation by distillation | amount treated | normal alkane g/hr | 27 |
| | amount of steam | (g/normal alkane-g) | 3.5 |
| | temperature | (° C) | 100 |
| | removal rate of sulfur dioxide | (%) | 100 |
| | pressure | (mmHg) | 50 |
| Separation of sulfuric acid | temperature | (° C) | 100 |
| | concentration of separated sulfuric acid | (wt %) | 70 |
| | time for separation of sulfuric acid | (min) | 10 |
| | separation rate of sulfuric acid | (%) | 90 |
| Properties of separated sulfonic acids | sulfonic acids content | (wt %) | 80 |
| | normal alkane content | (wt %) | 0.4 |
| | sulfuric acid content | (wt %) | 2.5 |
| | water content | (wt %) | 17.1 |
| | sulfur dioxide content | (wt %) | Only a trace observed. |
| | color (KL color 5 % sodium sulfonate aq. soln) | | 250 |

EXAMPLE 4

By means of employing a reaction mixture produced through the same operation as in Example 1, supplying said reaction mixture to the distillation tower 9, 5 cm in diameter and 30 cm in height, through the conduit 8, and introducing steam superheated at 110° C into said distillation tower through the conduit 10 while maintaining the inner pressure of the tower at 100 mmHg and further applying heat from the outside of the tower, steam-distillation was effected. Through the conduit 11, the distillate comprising normal alkane, water and sulfur dioxide was sent in the separation tank 12, where said distillate was separated into sulfur dioxide, normal alkane and water. Sulfonic acids, together with sulfuric acid of a concentration of 70 Wt.%, were made to flow out through the conduit 16, and the sulfonic acids were separated from said sulfuric acid within the separation tank 17. Thus obtained sulfonic acids were subsequently neutralized in the neutralization tank 19, whereby there were obtained alkyl sulfonates.

The conditions for conducting the experiment in this example together with the result of experiment were as shown in the following Table 6.

Table 6

| Process | Condition | | Result |
|---|---|---|---|
| Separation by distillation | amount treated | (normal alkane g/hr) | 27 |
| | amount of steam | (g/normal alkane-g) | 3.5 |
| | temperature | (° C) | 110 |
| | removal rate of sulfur dioxide | (%) | 100 |
| | pressure | (mmHg) | 100 |
| Separation of sulfuric acid | temperature | (° C) | 110 |
| | concentration of sulfuric acid | (wt %) | 70 |
| | time for separation of sulfuric acid | (min) | 10 |
| | separation rate of sulfuric acid | (%) | 90 |
| Properties of separated sulfonic acids | sulfonic acids content | (wt %) | 80 |
| | normal alkane content | (wt %) | 0.5 |
| | sulfuric acid content | (wt %) | 2.6 |
| | water content | (wt %) | 16.9 |
| | sulfur dioxide content | (wt %) | Only a trace observed |
| | color (KL color 5 % sodium sulfonate aq. soln) | | 250 |

COMPARATIVE EXAMPLE

The reaction mixture produced through the same operation as in the present Example 1 was first heated to remove sulfur dioxide therefrom, and was heated again thereafter to effect concentration of sulfuric acid contained therein. Subsequently, after removing thus concentrated sulfuric acid therefrom, the reaction mixture was neutralized and supplied to the distillation tower 9 shown in the appended drawing, where it was subjected to steam-distillation. The result of this experiment on separation of normal alkane was as shown in the following Table 7.

Table 7

| Process | Condition | | Result |
|---|---|---|---|
| Removal of $SO_2$ by heating | temperature | (° C) | 100 |
| | removal rate | (%) | 100 |
| Concentration of sulfuric acid | temperature | (° C) | 140–150 |
| | concentraton of separated sulfuric acid | (wt %) | 65–70 |
| Separation of sulfuric acid by settling | time for separation of sulfuric acid | (min) | 30 |
| | separation rate of sulfuric acid | (%) | 88 |
| Distllation (distillation of alkane) | amount treated | (normal alkane g/hr) | 11 |
| | temperature | (° C) | 150 |
| | amount of steam | (g/normal alkane-g) | 9 |
| Properties of separated sodium sulfonate | sodium sulfonate content | (wt %) | 60 |
| | sodium sulfate content | (wt %) | 3.5 |
| | normal alkane content | (wt %) | 0.5 |
| | water content | (wt %) | 36 |
| | color (KL color 5 % sodium sulfonate aq. soln) | | 400 |

What we claim is:

1. A process for recovering a purified reaction product comprised predominantly of alkyl sulfonic acid, from a reaction mixture obtained by photosulfoxidation of an alkane having a carbon atom number in the range of from 10 to 26, said reaction mixture containing $SO_2$, $H_2SO_4$, alkyl sulfonic acid, unreacted alkane and water, which process comprises the steps of:
   1. separating, by settling, the reaction mixture into an upper layer (a) of the unreacted alkane and a lower layer (b) consisting of the remainder of the reaction mixture;
   2. feeding lower layer (b) into a distillation vessel and feeding steam directly into the charge of (b) in the distillation vessel to effect distillation of said charge at a temperature in the range of from 80° to 250° C and a pressure in the range of from 50 to 760 mmHg and thereby obtaining a distillate fraction (c) containing substantially all the remaining unreacted alkane, substantially all the $SO_2$ and water, and a bottom fraction (d);
   3. separating, by settling and without supplying further heat, fraction (d) into a lower layer (e) of a concentrated aqueous solution of $H_2SO_4$ and an upper layer (f) comprised predominantly of alkyl sulfonic acid, constituting the purified reaction product.

2. A process according to claim 1, further characterized in that the distillation is effected at a temperature within a range of from 100° to 110° C and at a pressure within a range of from 50 mmHg to 100 mmHg.

3. A process according to claim 1, further characterized in that the concentration of the sulfuric acid in (e) is in range of from 50 to 95% by weight.

4. A process according to claim 1, further characterized in that the concentration of the sulfuric acid in (e) is in range of from 65 to 80% by weight.

* * * * *